US012008757B2

(12) United States Patent
Karki et al.

(10) Patent No.: US 12,008,757 B2
(45) Date of Patent: Jun. 11, 2024

(54) METHOD AND SYSTEM FOR AUTOMATIC MULTIPLE LESION ANNOTATION OF MEDICAL IMAGES

(71) Applicant: Caide Systems, Inc., Lowell, MA (US)

(72) Inventors: Manohar Karki, North Billerica, MA (US); Jung Hwan Cho, Dracut, MA (US); Kye Wook Lee, Groton, MA (US)

(73) Assignee: Caide Systems, Inc., Lowell, MA (US)

( * ) Notice: Subject to any disclaimer, the term of this patent is extended or adjusted under 35 U.S.C. 154(b) by 388 days.

(21) Appl. No.: 17/432,248

(22) PCT Filed: Jan. 24, 2020

(86) PCT No.: PCT/US2020/014884
§ 371 (c)(1),
(2) Date: Aug. 19, 2021

(87) PCT Pub. No.: WO2020/154562
PCT Pub. Date: Jul. 30, 2020

(65) Prior Publication Data
US 2022/0254022 A1    Aug. 11, 2022

Related U.S. Application Data

(60) Provisional application No. 62/796,173, filed on Jan. 24, 2019.

(51) Int. Cl.
G06T 7/00     (2017.01)
G06T 7/136    (2017.01)
G06V 10/82    (2022.01)

(52) U.S. Cl.
CPC ............ *G06T 7/0014* (2013.01); *G06T 7/136* (2017.01); *G06V 10/82* (2022.01); *G06T 2207/10081* (2013.01); *G06T 2207/10088* (2013.01); *G06T 2207/20081* (2013.01); *G06T 2207/20084* (2013.01); *G06T 2207/30096* (2013.01)

(58) Field of Classification Search
CPC ......... G06T 7/0014; G06T 7/136; G06T 7/00; G06T 2207/30096; G06T 2207/20081; G06T 2207/20084; G06T 2207/10081; G06T 2207/10088; G06V 10/82
See application file for complete search history.

(56) References Cited

PUBLICATIONS

B. Kayalibay et al. CNN-Based Segmentation of Medical Imaging Data. arXiv preprint arXiv:1701-03056, 2017 [online] [retrieved on Apr. 15, 2020]. Retrieved from: <https://arxiv.org/abs/1701.03056>, chapters 1, 3.2.3, 4.1, 4.2, 5.2, fig 14.

Chartsias, Agisilaos et al. Multimodal MR Syntesis via Modality-Invariant Latent Representation. IEEE transactions on Medical Imaging vol. 37,3 (2018): 803-814 [ online] [retrieved on Apr. 15, 2020]. Retrieved from: <https://www.ncbi.nlm.nih.gov/pmc/articles/PMC5904017>, chapters II, VI, subchapter H, fig 10.

(Continued)

*Primary Examiner* — Tuan H Nguyen
(74) *Attorney, Agent, or Firm* — Occhiuti & Rohlicek LLP

(57) ABSTRACT

A method includes receiving, from a patient, an image having a visible lesion, modifying the image to appear as if the lesion were not present, thereby forming a second image, generating a delineation of the abnormality using a difference between the first and second images, and tagging the segmented lesions.

19 Claims, 11 Drawing Sheets

(56) References Cited

PUBLICATIONS

X. Chen, E. Konukoglu. Unsupervised Detection of Lesions in Brain MRI Using Constrained Adversarial Auto-Encoders, arXiv preprint arXiv:1806.04972, 2018 [online] [retrieved on Apr. 14, 2020]. Retrieved from: <https://arxiv.org/abs/1806.04972>, abstract.

Marcus, Daniel S. et al. Open Access Series of Imaging Studies (OASIS): Cross Sectional MRI Data in Young, Middle Aged, Non0demented, and Demented Older Adults. Journal of Cognitive Neuroscience (2007) [online] [retrieved on Apr. 15, 2020]. Retreived from: <https://dash.harvard.edu/handle/1/33896768>, p. 1499. 1501-1504.

Liang-Chieh Chen et al. Semantic Image Segmentation with Deep Convolutional Nets and Fully Connected CRFs. 2016 [online] [retrieved on Apr. 15, 2020]. Retrieved from: <https://arxiv.org/abs/1412.7062>, abstract, chapters 3, 4.1, 4.2.

METHOD AND SYSTEM FOR AUTOMATIC MULTIPLE LESION ANNOTATION OF MEDICAL IMAGES

CROSS-REFERENCE TO RELATED APPLICATIONS

This application is a national phase under 35 U.S.C. 371 of International Application No. PCT/EP2020/014884 filed on Jan. 24, 2020, which claims priority to U.S. Application No. 62/796,173 filed on Jan. 24, 2019, the contents of all of which are hereby incorporated by reference in their entireties.

RELATED APPLICATIONS

This application claims the benefit of the Jan. 24, 2019 priority date of U.S. Provisional Application 62/796,173, the contents of which are herein incorporated by reference.

FIELD OF THE INVENTION

The invention relates to medical imaging and in particular to methods and systems for facilitating the analysis of medical images.

BACKGROUND OF THE INVENTION

A variety of ways exist to non-invasively obtain medical images. These include magnetic resonance imaging and computerized tomography.

Using such images, it is possible to identify lesions in various places that would otherwise be difficult to inspect directly. In particular, such methods can be used to inspect the brain.

In the course of inspecting an image of the brain, one sometimes finds lesions. The significance of such lesions varies as a function of morphology and location. Thus, it is useful to accurately characterize these lesions to promote more accurate diagnosis.

Although non-invasive imaging is a useful way to detect lesions in the brain, it is somewhat difficult to accurately characterize these lesions. Known methods of doing so are tedious and error-prone.

Advances in deep-learning technology have improved the performance of classification and segmentation tasks in medical image analysis. Nevertheless, obtaining large amounts of medical imaging data for training deep convolutional neural networks is expensive. In addition, it is time-consuming to carry out the annotation task to delineate target lesions and define annotation ground truth labels. Since this task requires human intervention, the results can be inconsistent depending on differences between the humans charged with carrying out these tasks. Hence, deep learning performance can vary significantly depending upon on the acquired labeled data. Supervised methods for segmenting and annotating these images need large amounts of data.

SUMMARY OF THE INVENTION

The subject matter described herein supplants the tedious and expensive process of labelling and annotating data to promote segmentation and annotation of abnormal regions in medical images. The methods and systems described herein provide for automatically identifying segments and annotating abnormal lesion in medical images. Some embodiments avoid having to apply any spatial transformations to the images. Among the embodiments are those that carry out automatic annotation of abnormal regions by extracting an initial segmentation with a generative adversarial neural network and postprocessing and outlining the segmentation.

The methods and systems described herein provide ways to segment and outline abnormal regions in medical images with little or no prior information about the content of the images. The approach uses images that are classified as normal and abnormal. As used herein, "abnormal" includes images that contain subject matter of interest.

In one aspect, the invention features a system that differentiates the two types of images and highlights the differences on the abnormal images. Among the embodiments are those that include components for retrieving the data and creating a dataset to train an auto annotation system component.

The invention relies in part on an automatic annotation system that, once trained, stores specific models for specific body anatomy. The annotation system comprises an adversarial deep neural network that has been trained with abnormal and normal images. The adversarial deep neural network at first outputs two images. One of these images, hereafter referred to as the "first" image, is derived by starting with an image that shows a lesion and reconstructing the image to replace the lesion with a patch. As a result, this first image appears to be a normal image. The other image, hereafter referred to as the "second" image, contains only lesion. The lesion and the patch are at the same location.

Some practices feature adding this segmented patch from the second image to the first image, for example by adding corresponding pixel to pixel values. This results in a reconstructed version of the original abnormal image. Examples of post processing steps that can be applied to the segmented patch includes binarization to create a mask and morphological image processing to remove noise and fill missing pixels.

The adversarial nature of the system arises from an attempt to classify the first output image as being either a normal image or an image that has been synthetically altered to look like a normal image. Errors in this classification provide a basis for improving the synthetic alteration process.

As the synthetic alteration process improves, the change from the abnormal to normal image is captured by the second output image, which also represents the abnormal part of the abnormal image. This reconstruction process incurs a reconstruction cost that discourages a generative component of the network from making major modifications to the abnormal image in an attempt to make it look like a normal image. This inhibits changes to any normal regions of to the abnormal image. It also promotes modifications to only the abnormal regions of the abnormal image.

In some embodiments, an image retrieval component receives the electronic medical record information based on a query that includes identifiers for a disease, a patient, and a portion of the anatomy that is of interest. The image retrieval component sends a request to a picture archiving and communication system for the patient's image data. The retrieved patient data along with electronic medical record data is used to classify patient data is normal or abnormal. This classification results in two data sets that can be used for training an automatic annotation system. In some embodiments, the image retrieval component stores the trained model for the body anatomy in model storage.

An alternative practice avoids automatic annotation and instead relies on experts who classify data as normal and abnormal. In either case, the data thus classified is used for training.

Another aspect of the invention features a method for annotating medical processes images in a database of medical images. The database includes first and second sets of images. Images in the first set are known to have lesions. Images in the second set are known to be free of lesions.

The processing of stored images in the database determines values of parameters for configuring image analysis components. This includes determining values of parameters of a first image analysis component and values of parameters of a second image analysis component.

The first image analysis component is configured to receive an input image as its input and to provide, as one of its outputs, a synthetic image. The first image analysis component forms the synthetic image from the input image. It does so by reconstructing that portion of the image that contains the lesion so that the image takes on the characteristics of a normal image. The resulting image is thus a synthetic normal image.

The first image analysis component's other output is lesion data. This lesion data characterizes the lesion region that has been reconstructed.

The second image analysis component is configured to discriminate between normal images and a synthetic image. The normal images come from an externally-provided set of normal images. The synthetic image is that provided by the first image analysis component.

The values of the parameters are selected to both hinder the second image analysis component's ability to discriminate between a synthetic image and the normal images and to promote the ability to reconstruct an image from a set of abnormal images based on the outputs of the first image analysis component.

Some practices also include causing the first image analysis component to process each image from the set of abnormal images. This processing is such as to generate annotated images based on lesion data produced by the first image analysis component with a first abnormal image as an input thereof.

In some embodiments, the first image analysis component includes an encoder and a decoder. In such embodiments, the encoder has a lower resolution than the decoder. This lower resolution is manifested, in some embodiments, as a lower spatial resolution or a smaller number of signal values at an output of the decoder. In some embodiments, this results in a 256×256 input image being reduced to a 16×16 image at the encoder's output. The decoder thus takes the lower resolution output of the encoder and generates a synthetic image at the resolution of the encoder's input.

In some practices, the process of determining the values of the parameters is carried out iteratively. This includes iteratively updating values in each iteration.

Some practices feature having the first image analysis component process a first abnormal image. The result of such processing is a synthetic image obtained from the first abnormal image and lesion data for the first abnormal image. The second image analysis component is then provided with an image that is either the synthetic image or a normal image. It then attempts to determine whether the unknown image is synthetic or not.

In some practices, processing the first abnormal image includes processing the synthetic image and the lesion data to produce a synthetic abnormal image. This is followed by determining an extent to which the first abnormal image and the synthetic abnormal image differ.

Practices further include those in which the lesion data characterizes a spatial extent of the lesion region. Among these are practices in which the lesion data includes an outline and practices in which the lesion data includes a binary mask.

Other practices include those in which the lesion data includes image data in the lesion region. Among these are practices in which the lesion data include data at the resolution of the input abnormal image.

Embodiments include those in which both the first and second image processing components include an artificial neural network. In some of these embodiments, the process of determining values of the parameters includes performing an adversarial training procedure using a combined metric. The combined metric is one that represents both an overall ability to discriminate between images from the set of normal images and synthetic normal images provided by the first image analysis component and also an ability to reconstruct images from the set of abnormal images using outputs of the first image analysis component.

In another aspect, the invention include a non-transitory computer-readable having encoded thereon software that, when executed by a data processing system, carries out any of the foregoing processes.

In yet another aspect, the invention features a data processing system configured to carry out any of the foregoing processes.

In yet another aspect, the invention features an automatic annotation system comprising a combination of a hybrid network that includes an adversarial deep neural network and an anatomical normalization module, a natural-language processing module, and an iterative neural network.

All methods and systems described herein are of the non-abstract variety. As such, all claims presented herein recite non-abstract subject matter and only non-abstract subject matter. Any person who construes the claims as covering abstract subject matter would therefore have done so incorrectly and, in doing so, would have failed to construe the claims in light of the specification as required by law. Applicant, acting as his own lexicographer, hereby defines "non-abstract" as describing subject matter that is covered by 35 USC 101 as of the filing date of this application. A description of an abstract implementation using abstract components has been purposefully omitted to ensure no misunderstanding.

All methods and systems described herein are of the technical variety. As such, all claims presented herein recite technical subject matter and only technical subject matter. A description of a non-technical implementation using non-technical components has been purposefully omitted to ensure no misunderstanding. Any person who construes the claims as covering abstract subject matter would therefore have done so incorrectly and, in doing so, would have failed to construe the claims in light of the specification as required by law.

These and other features of the invention will be apparent from the following detailed description and the accompanying figures, in which:

DETAILED DESCRIPTION OF PREFERRED EMBODIMENTS

Figure 1:
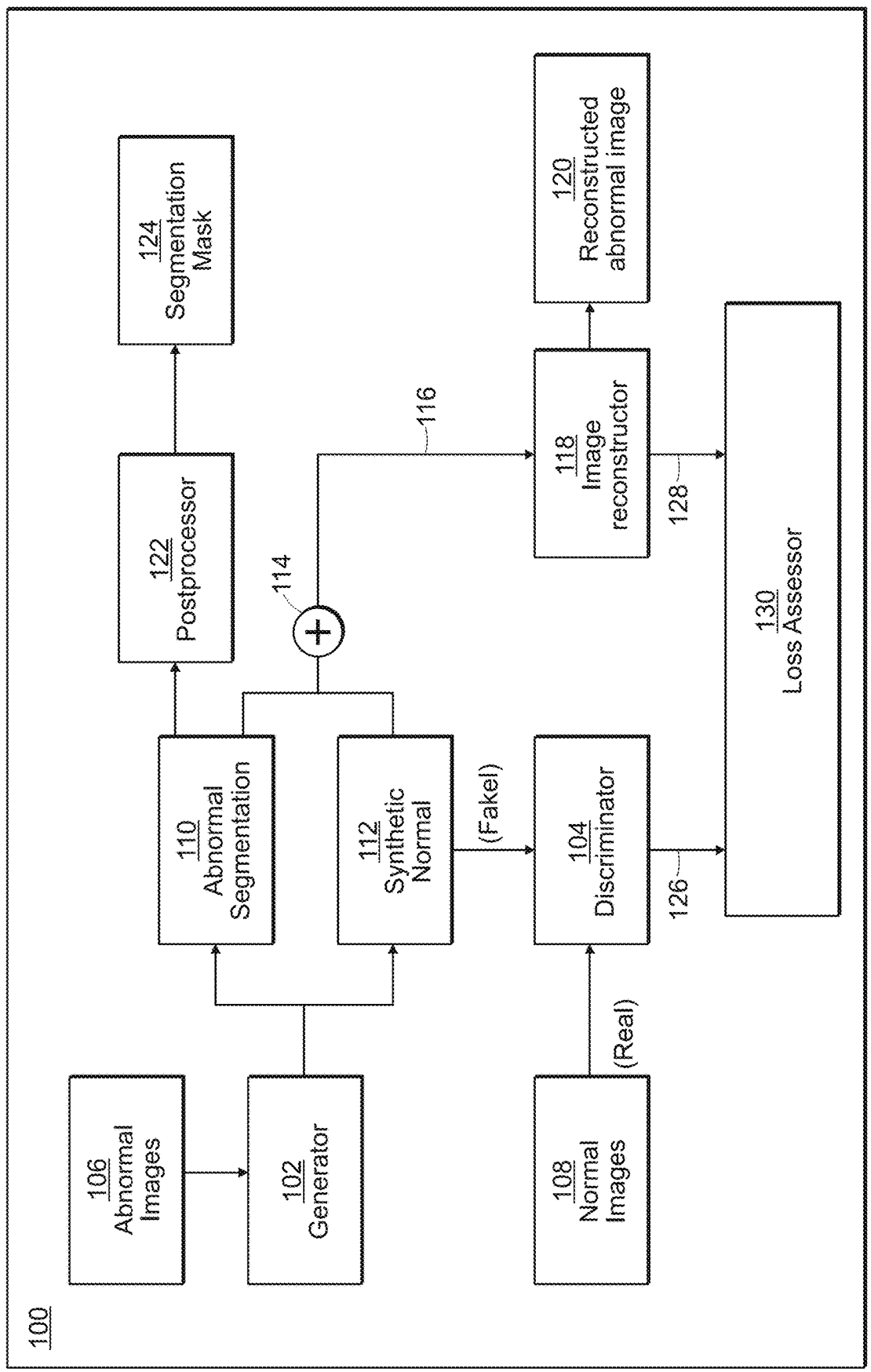
FIG. 1 is a block diagram of an embodiment of an adversarial deep neural network.

FIG. 1 shows an adversarial deep neural network 100 having a generator 102 and a discriminator 104, both of which are neural networks themselves. The generator 102 receives abnormal images 106 as inputs. The discriminator 104 receives normal images 108 as inputs.

The generator 102 and the discriminator 104 have been trained to carry out different tasks. In particular, the generator 102 has been trained to use an abnormal image 106 as a basis for outputting an abnormal segmentation map 110 and a synthetic normal image 112. In contrast, the discriminator 104 has been trained to improve its ability to distinguish between the real normal images 108 and the synthetically produced image 112 provided by the generator 102.

To generate the synthetic normal image 112 from the abnormal image 106, the generator 102 modifies the abnormal image 106. It does so by removing a distinct region of the abnormal image 106 that corresponds to the abnormality. A residual part of the abnormal image 106 that has thus been removed from the abnormal image 106 forms the basis of the abnormal segmentation map 110.

A combiner 114 combines the synthetic normal image 112 and the abnormal segmentation 110, or "lesion map," to generate a combined image 116. An image reconstructor 118 uses the combined image 116 to yield a reconstructed original abnormal image 120.

Meanwhile, a postprocessor 122 uses the abnormal segmentation map 110 to generate a segmentation mask 124 for segmenting one or more abnormal regions.

Training a neural network imposes a training cost. In the adversarial deep neural network 100, there exist discrimination costs 126 associated with discriminating between real and synthetic images and reconstruction costs 128 associated with the operation of the image reconstructor 118. These are provided to a loss assessor 130.

The loss assessor 130 assesses costs associated with training the discriminator 104 to reliably classify an image as being a real image or a fake image. In the illustrated embodiment, the loss assessor 130 computes the Wasserstein Loss with gradient penalty. This is particularly useful for calculating training loss when training a generative adversarial network.

The loss assessor 130 also evaluates losses associated with having the generator 102 make significant modifications to an abnormal image 101. To evaluate this loss, the second loss assessor 107 receives as an output of an error determination unit 140 that receives an original abnormal image 106 and a reconstructed abnormal image 120 and outputs some indicator of a difference between them. In the illustrated embodiment, that indicator is the mean square error between them.

Figure 2:
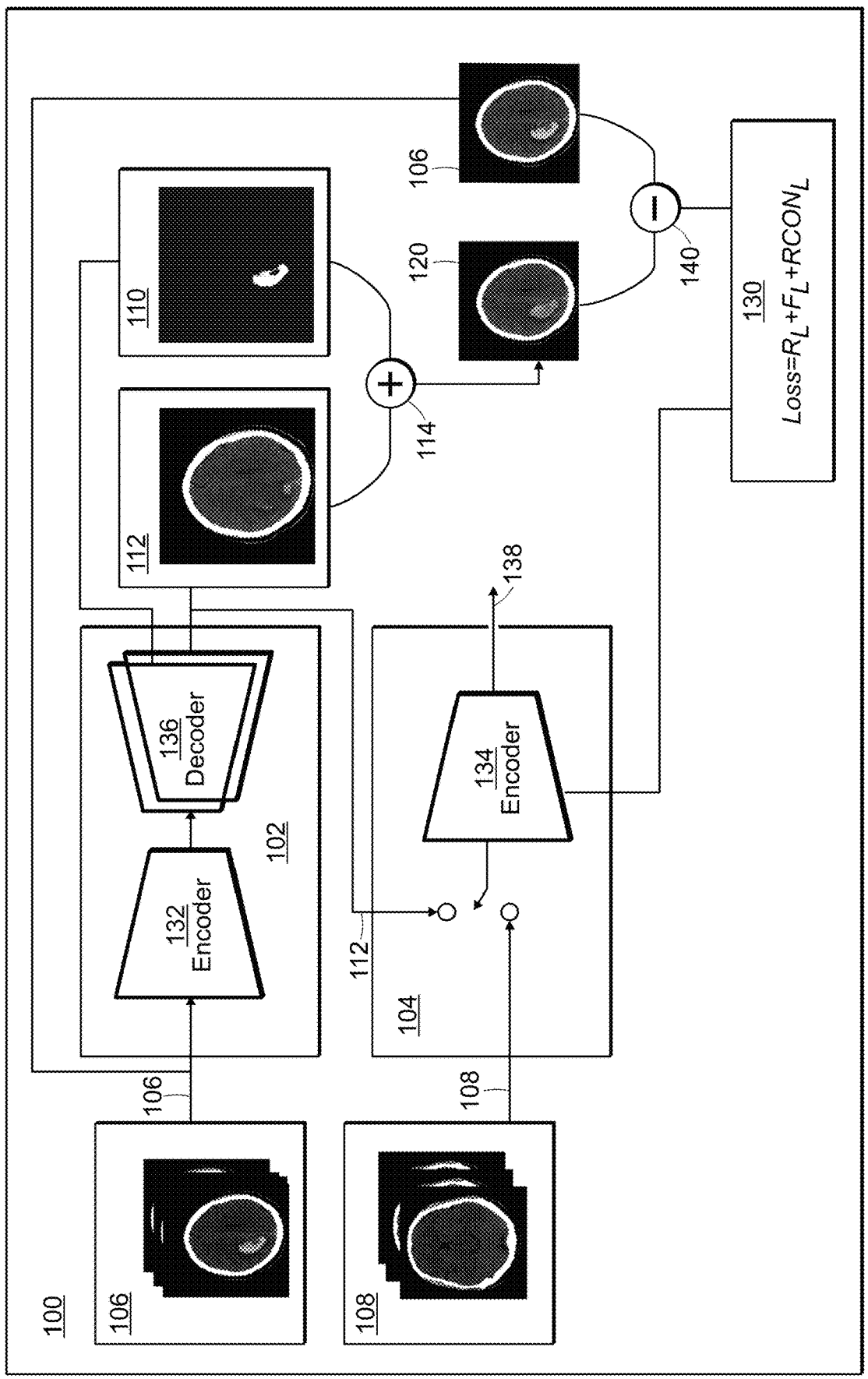
FIG. 2 illustrates the use of the network of FIG. 1 for tomographic images of a brain.

Referring now to FIG. 2, the adversarial deep neural network 100 includes first and second encoders 132, 134 and a decoder 136. The first encoder 132 and the decoder 136 are constituents of the generator 102. The second encoder 134 is a constituent of the discriminator 104.

The second encoder 134 switches between receiving a real normal image 108 and a synthetic normal image 112. It then outputs a binary value 138 indicative of whether it regards the image that it has received as being the real normal image 108 or the synthetic normal image 112. In the illustrated embodiment, the real images 108 are tomographic images of a brain and the real abnormal images 106 are tomographic images of brains with lesions.

The abnormal images 106 showing lesions are passed to the encoder 132, which provides them to the first decoder 136. The first decoder 136 creates the synthetic normal image 112 and an abnormal segmentation map 104, or lesion mask. A combiner 122 combines the synthetic normal image 112 and the lesion mask 104 to yield the reconstructed image 124.

The loss assessor 130 determines the total loss for the entire training as the sum of losses for classification of real images ($R_L$), losses for classification of fake images ($F_L$) and the reconstruction losses ($RCON_L$), the latter being a mean square error that arises from differences between reconstructed images 120 and original abnormal images 106.

Figure 3:
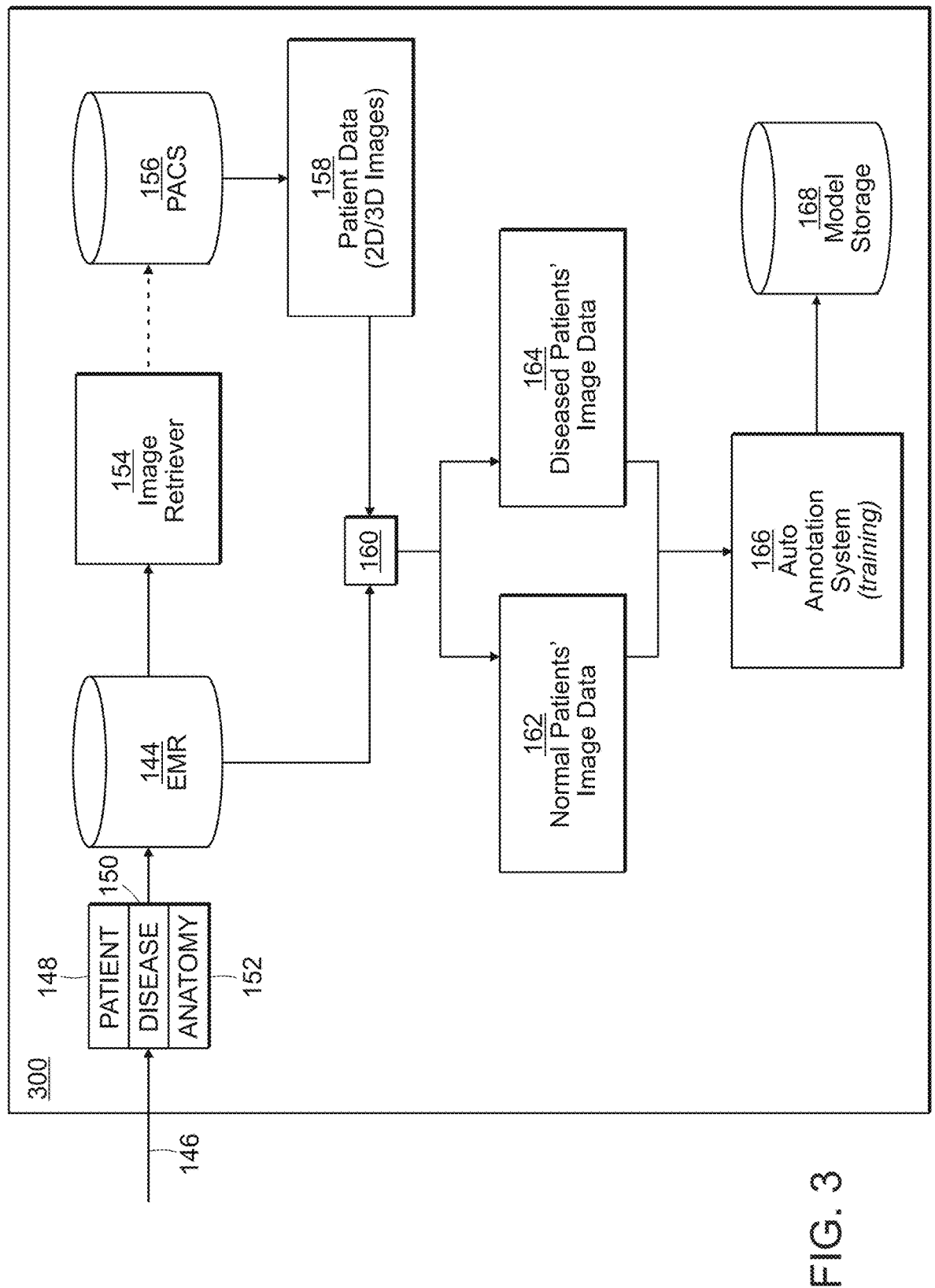
FIG. 3 is a flowchart diagram of data acquisition, preprocessing, training and storage of the trained model.

FIG. 3 demonstrates the training procedure 142 for automatic abnormal region segmentation and the workflow of the system.

The process begins with a user querying a database 144 of electronic medical records. This includes providing a query 146 that includes a first identifier 148, which identifies a patient, a second identifier 150, which identifies a disease, and a third identifier 152, which identifies that portion of a human's anatomy that is of interest.

An image retriever 154 interfaces with a picture archiving and communication system 156 to retrieve relevant image data 158, which can include two-dimensional or three dimensional-images. Then, based on the query 146, an image-preparation unit 160 classifies the images from the image data 158 are classified as normal images 162 and abnormal images 164 and then uncouples them from any patient identifiers, thus ensuring anonymity. The resulting anonymized images, which include both the normal and abnormal images 162, 164, form a training data set for an automatic annotation system 166.

The automatic annotation system 166 invokes the adversarial deep neural network 100 for training. Once trained, the resulting model is saved to the model storage database 166. A wide collection of models trained for identification of different types of abnormalities i.e. diseases in different parts of the human anatomy, are stored in the model storage database 168. New models can be added to the model storage database 168. In addition, existing models can be retrieved, either to be used or for further refinement.

Figure 4:
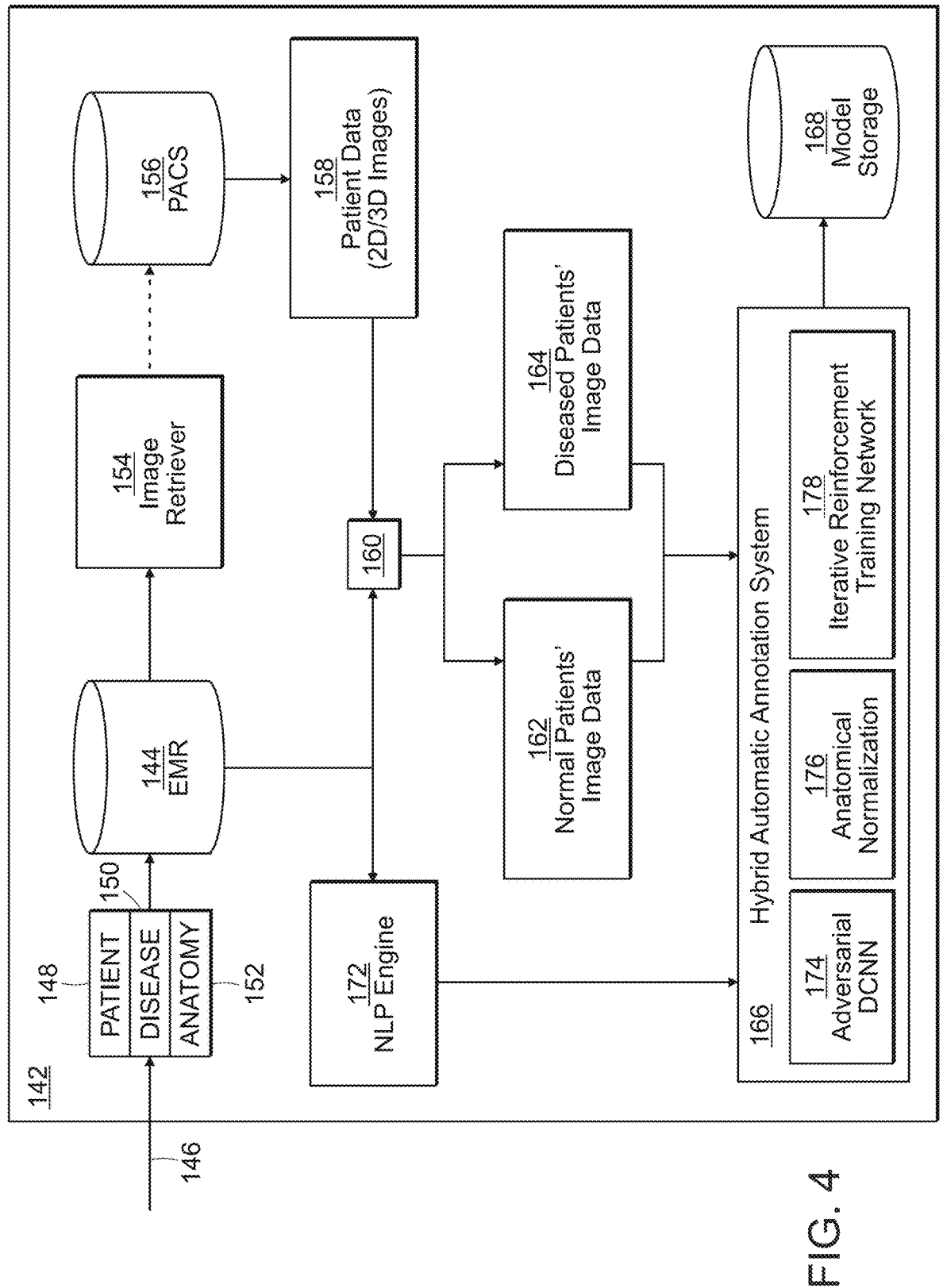
FIG. 4 shows an alternative embodiment of FIG. 3.

FIG. 4 demonstrates an alternative training procedure 142 for automatic abnormal region segmentation and the workflow of the system.

The alternative process proceeds in a manner similar to that shown in FIG. 3. However, embodiment includes a natural language processing engine 172 that communicates with both the image-preparation unit 160 and the database 144. The natural language processing engine 172 makes it possible to extract semantic keywords from the database 144, such as from a radiology report in the database 144.

In the embodiment of FIG. 4, the automatic annotation system 166 is a hybrid system that includes an adversarial deep convolution neural network 174, an anatomical normalization unit 176, and an iterative reinforcement training network 178.

The hybrid auto-annotation system 166 invokes the training module of the adversarial DCNN 174 and the anatomical normalization unit 176. Once each module is trained, initial seed annotation data set from the whole unlabeled image is generated. The seed labeled data set is incremented and refined by iterative reinforcement training network 178. The final trained model is then saved to the model storage database 168.

Figure 5:
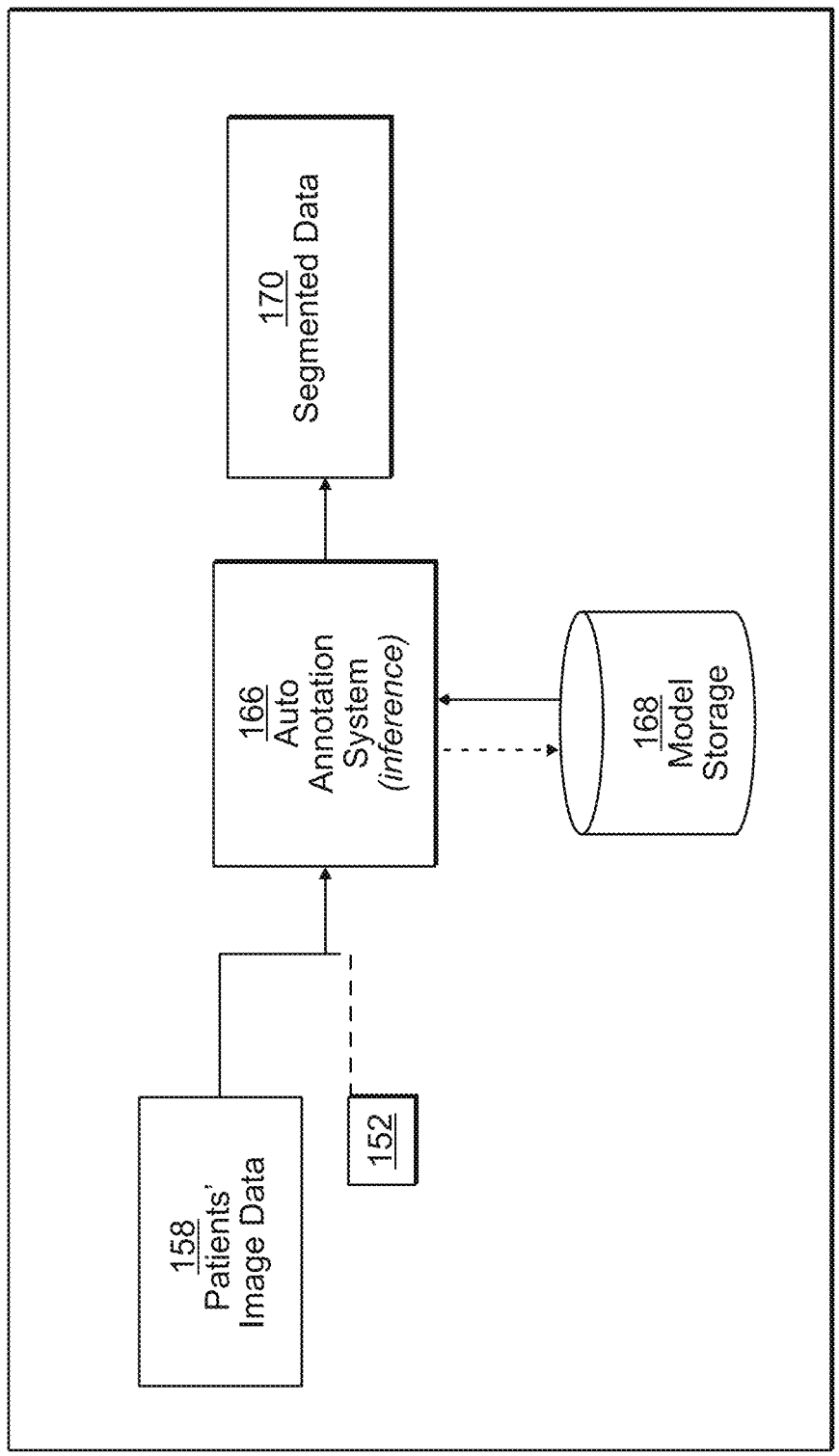
FIG. 5 is a flowchart diagram of usage of the automatic annotation system for segmentation of lesion on a patient's image.

Once the automatic annotation system 166 has been trained, it is put to use for inference, as shown in FIG. 5.

Referring now to FIG. 5, the automatic annotation system 166 receives, as one input, the third identifier 152, which is the one that identifies that portion of the human anatomy that is of interest. The automatic annotation system 166 also receives corresponding images from the patient's image data 158, which has been suitably anonymized.

After having received the relevant inputs, the automatic annotation system 166 retrieves an applicable model from the model storage database 168 and, after carrying out computation, outputs segmented images 170. Embodiments of the automatic annotation system 166 also include those that displays the outline annotation on the images, those that save the images, those that transfer the images to detailed classification modules, and those that carry out combinations of the foregoing.

Figure 6:
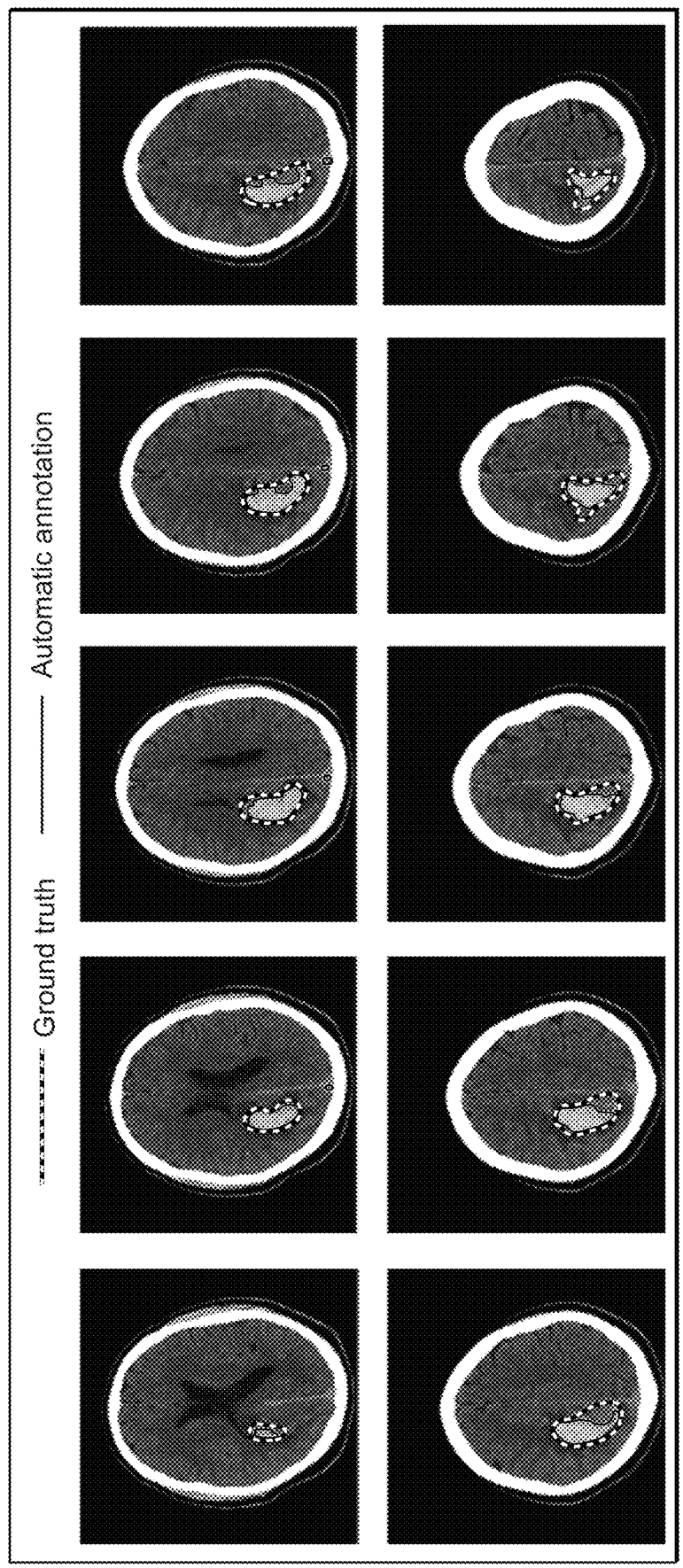
FIG. 6 illustrates examples of a patient's brain CT scans at different intervals, the ground truth of lesion segmentation and the automatically annotated segment.

FIG. 6 is an example of the result from the auto annotation system where Intraparenchymal hemorrhage (IPH) lesions are segmented. The red outline is the ground truth annotated by expert doctors and the blue annotation is the outline for the segmentation mask as predicted by the automatic annotation system.

Implementations of the approach(es) described above may make use of software stored on a non-transitory machined readable medium that is executed on a general-purpose or special purpose processor. The input and output images and other data related to the images may be stored in a database, which is accessed by the processor during execution.

Figure 7:
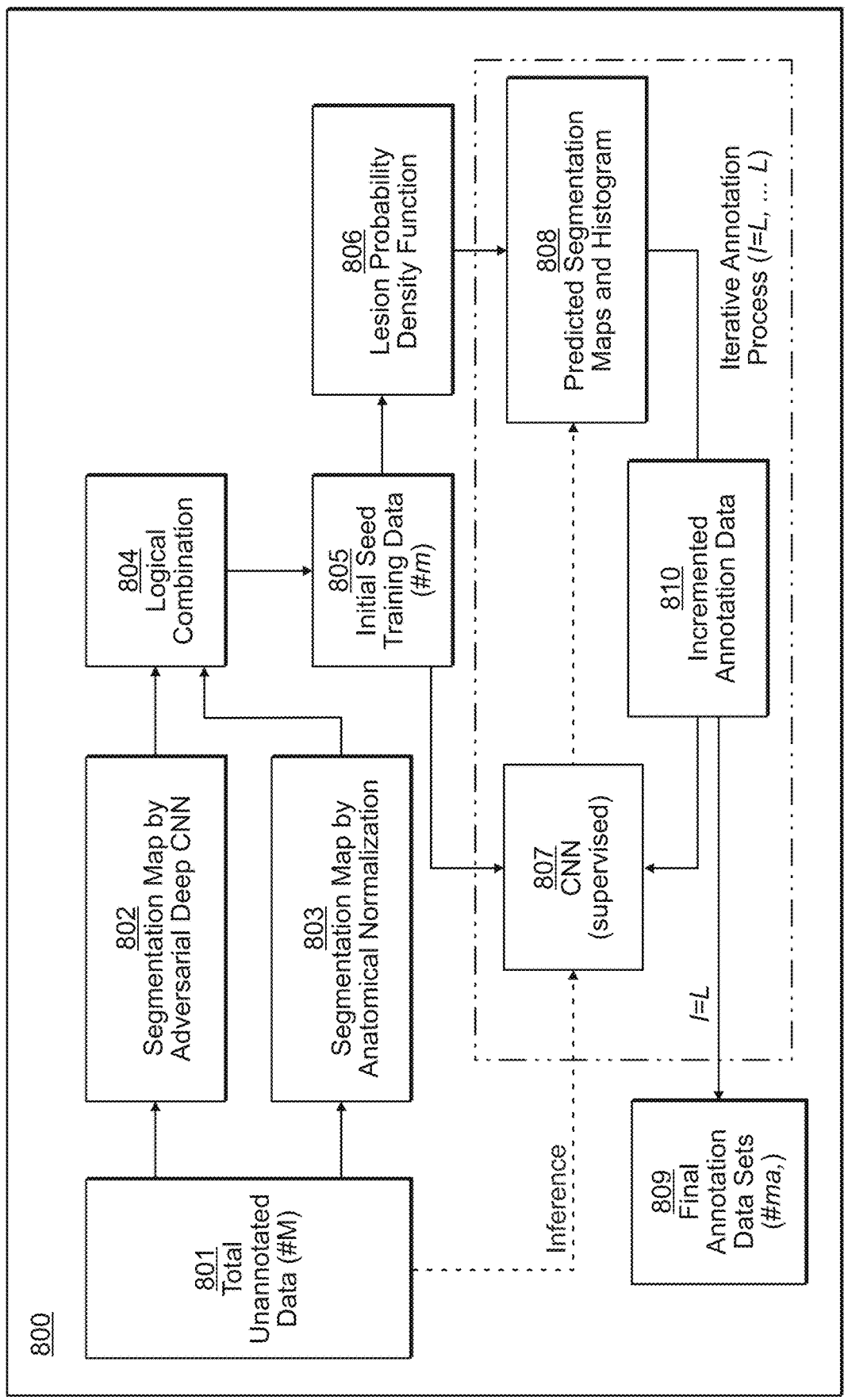
FIG. 7 illustrates an embodiment of iterative training network for incrementing the number of annotation and refining the annotated lesions.

FIG. 7 illustrates an iterative reinforcement training network 800 to increase the amount of annotation data and to refine the annotated lesions. Using the two trained modules, the segmentation maps 802 and 803 are obtained from the adversarial deep convolution neural network and anatomical normalization, respectively in given total unannotated data.

Combining predicted segmentation maps with an AND or OR logical operator 804 generates an initial annotation data set 805. For example, if two maps are combined by the AND operator, the annotated seed data produces readily apparent lesion maps.

The probability density function of each segmented map is estimated and the estimated density functions are averaged over the annotated seed data set. This results in a representative lesion probability density function 806.

First the convolution neural network segmenter 807 such as Inception-ResNet and DensNet is trained in supervision with the initial data set 805 (#m) and the trained convolution neural network is used to infer a total unlabeled data set 801 (#M).

To select a good quality of segmentation map, the representative lesion probability density 806 is applied to calculate a likelihood value of the predicted segmentation map 808. If the value is higher than a user defined value, the segmented data is added into an initial training data set.

The convolution neural network uses the incremented training data set 810 on the second training step (l=2) and the convolution neural network is iteratively trained until the number of annotation data is not any more increased (l=L). This results in the number of the annotation data items ($\#m_a$) 809 from the total of unannotated data items (#M).

Figure 8:
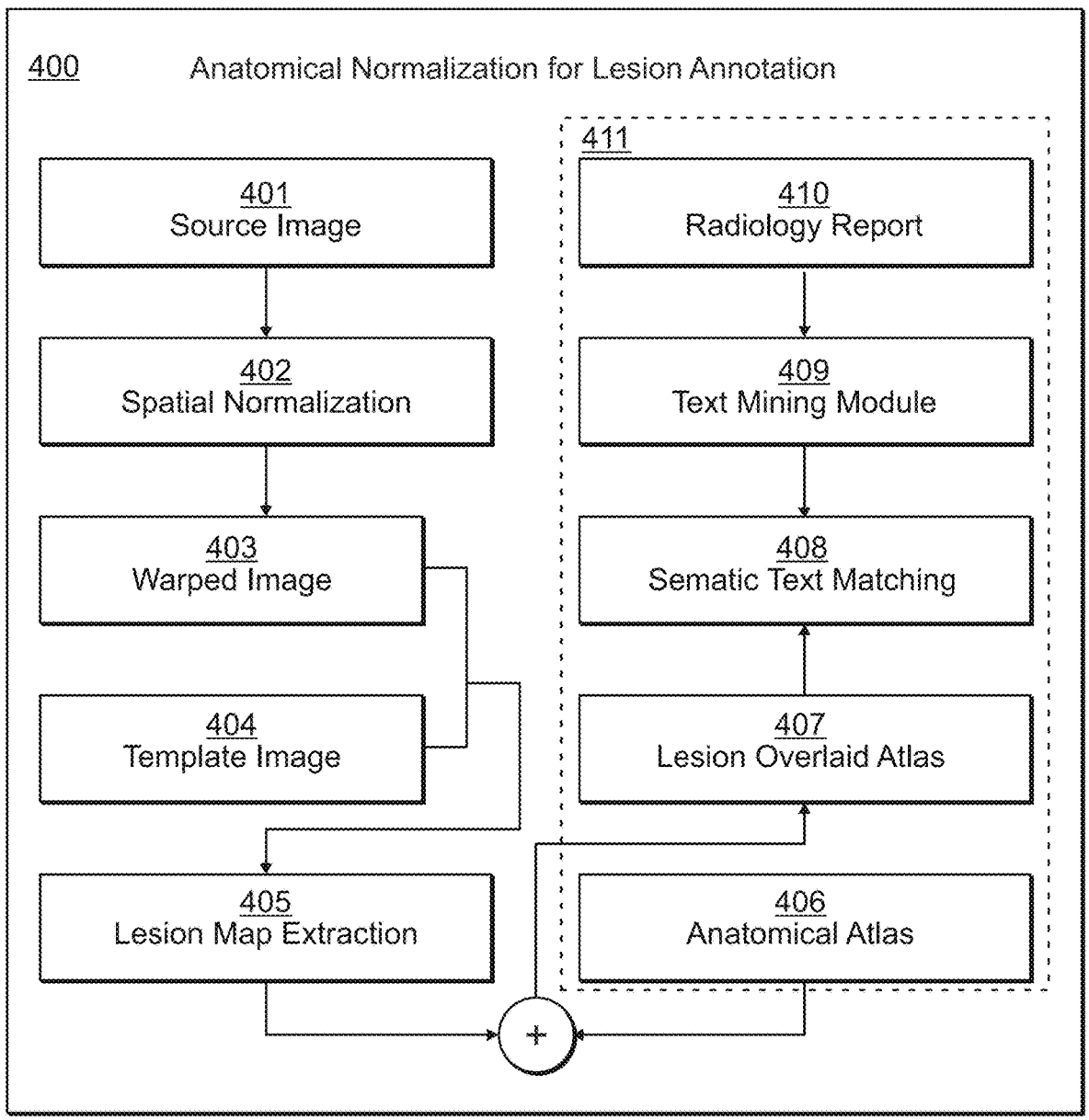
FIG. 8 is a flowchart diagram of an automatic lesion annotation by anatomical normalization.

FIG. 8 shows an implementation of an automatic lesion-extraction procedure that relies on a spatial normalizer 402, a template image 404, and an anatomical atlas 406.

The spatial normalizer 402 transforms a source image 401 into a template image 404 as a target. A normalized or warped image 403 is compared to normalized normal image as a control group and a lesion probability map 405 is extracted by statistical voxel comparison. The extracted lesion is overlaid on the anatomical atlas 406, which has been created by averaging the segmented anatomy of N healthy populations.

Construction of a lesion-labeled image is carried with a text-mining module 409. A suitable text-mining module 409 is one that implements statistical keyword extraction.

Figure 9:
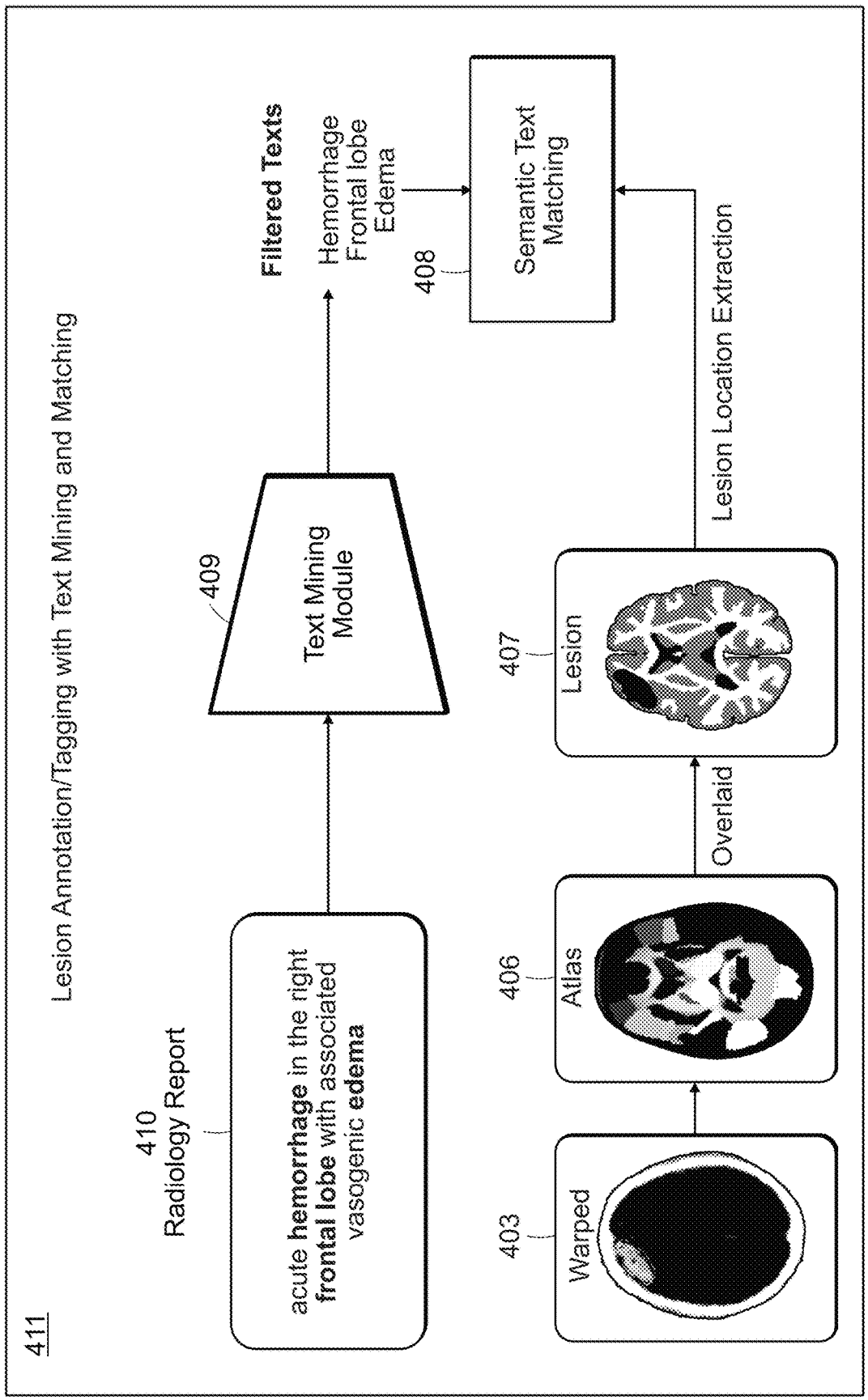
FIG. 9 is lesion annotation examples by text mining and sematic text matching between a radiology report and normalized lesion information.

A semantic text-matching module 408 matches a lesion-segmented image 407 with text from a radiology report 410 as shown in FIG. 9. The task of the semantic text-matching module 408 is simplified by having the radiology report 410 describe lesion ontology using a standard radiological lexicon. A useful standard lexicon has been compiled as "RadLex." The various labels that characterize lesion ontology can be categorized by the body part in which the lesion is found, the type of lesion, and the lesion's attributes. For example, a lesion may be identified as being in the brain, or more specifically, in the frontal lobe. Or a lesion may be identified as a bleeding lesion. Examples of lesion attributes include an extent of its hyperdensity or hypodensity.

The process further includes extraction of lesion-relevant information from the normalized lesions on the anatomical atlas 406. Since the anatomical atlas 406 was created by averaging the segmented anatomy of healthy populations, the overlaid lesion image 407 can extract the location information from the anatomical atlas 406 and extend the labels.

Finally, the lesion attributes from the anatomical atlas 406 are matched with the extracted keywords by calculating a similarity score based on a similarity between the keywords and the label annotation and establishing a relevance based on the similarity score. This includes carrying out text pre-processing to remove redundant text and to obtain normalized text corpus by lemmatization. A useful tool for carrying out this procedure is the Python NLTK library.

The text corpus is next tokenized and vectorized and saved in a bag-of-words model. A suitable tool for carrying out this procedure is CountVectoriser.

After refining the word counts with a TF-IDF vectorizer, keywords are extracted by their TF-IDF scores. Extraction of the lesion information normalized on the anatomical atlas 406 includes using two different atlases: the MNI structural atlas (nine region labels) for coarse-level anatomy segmentation and the Harvard-Oxford atlas (sixty-nine labels) for fine-grained anatomy labels. Since both atlases are constructed by registration to MNI152 spaces, the warped images are directly overlaid on the anatomical atlas 406 for extraction of relevant labels. In the particular example shown, which includes a hemorrhage lesion prototype, each lesion has been assumed to have three categorized labels: body part/location (same labels with brain atlas, i.e. 9 or 69 labels), lesion type (5 bleeding typed labels), and intensity (2 labels).

Figure 10:
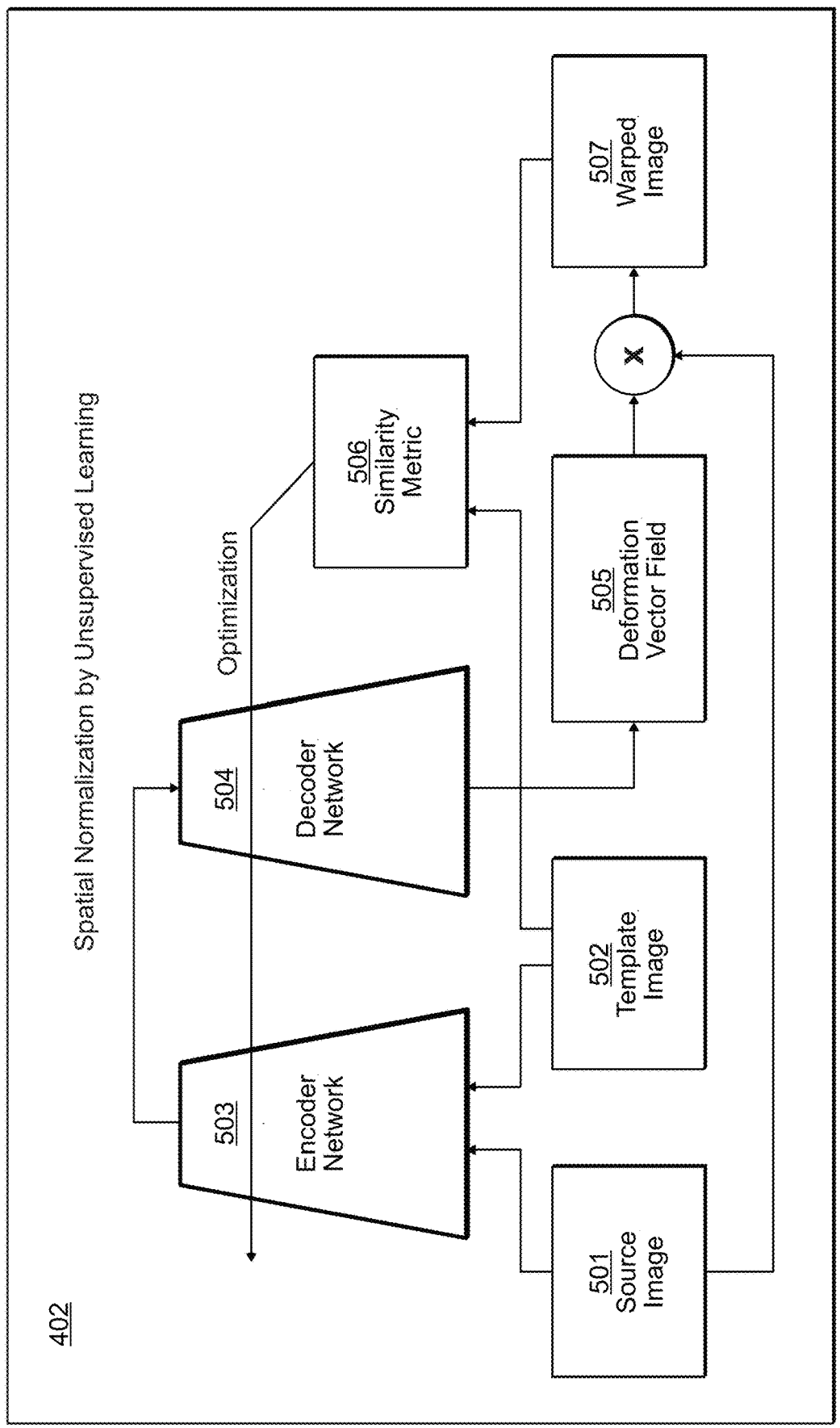
FIG. 10 illustrates an embodiment of a spatial-normalization procedure that uses a spatial transformation network.

FIG. 10 shows a system for carrying out spatial normalization to register a source image 501 to a template 502 by minimizing differences between them. The process of minimizing the differences includes warping the source image 501 using deformation vector fields that have been trained by an encoder network 503 and a decoder network 504. Mutual information or cross-correlation between the warped image 507 and a target template provide a similarity metric 506 that is indicative of similarity between the images.

A suitable encoder network 503 is a convolutional neural network that includes a standard form, an inception module, and a residual block. A suitable decoder network 504 is one that has been implemented using an approach that is opposite to that used to implement the encoder network 503. In particular, through an up-sampling scheme using a deconvolution or transposed convolution operator, the decoder network 504 produces a deformable field that enables a source image 501 to be register into a template image 502.

Additional and optional structures of the decoder network 504, such as skip connections and a pyramid pooling module, provide additional benefits in generating output at finer spatial scales and enabling more accurate anatomy registration.

Figure 11:
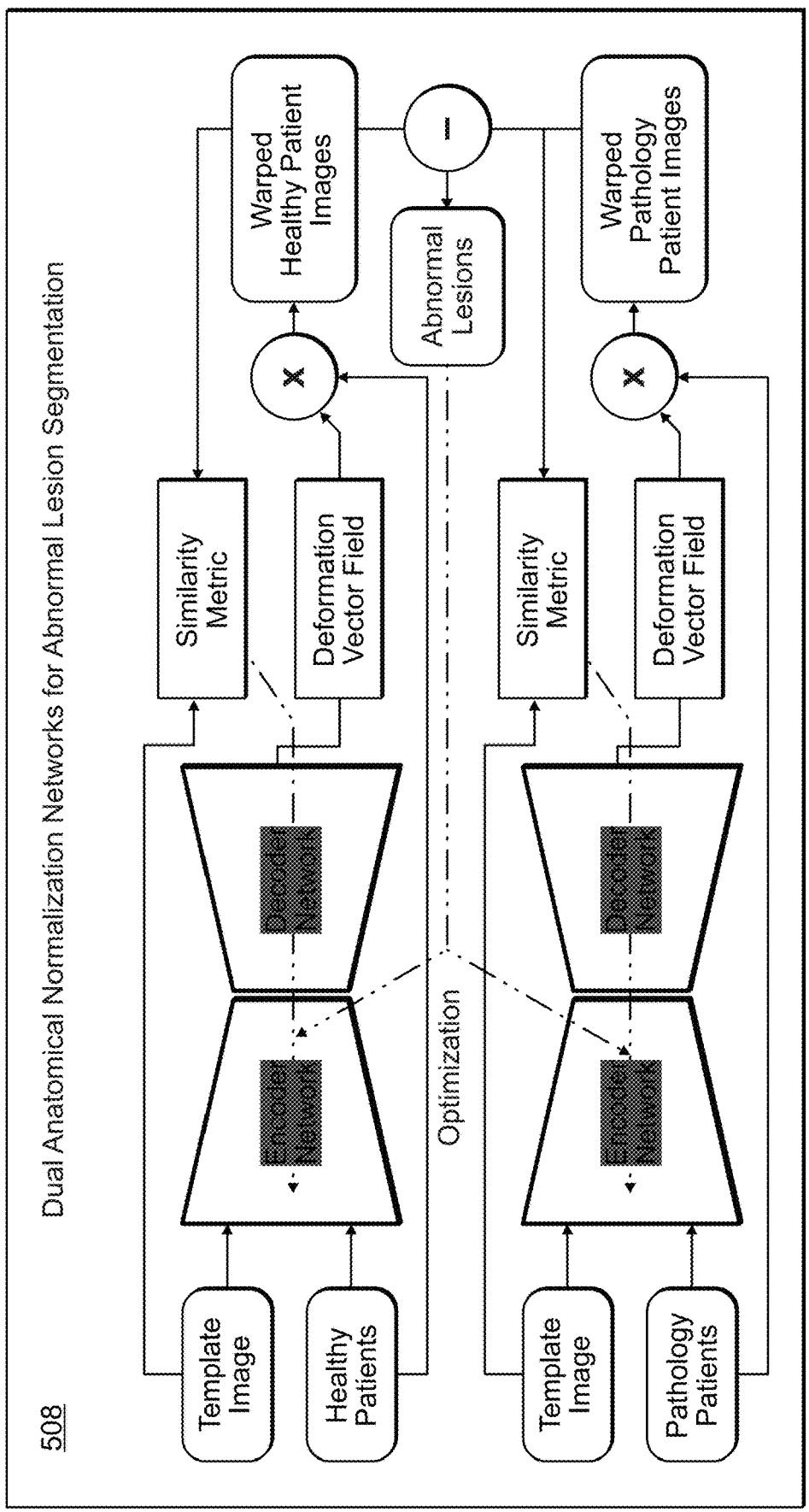
FIG. 11 illustrates an embodiment of dual-anatomy normalization-network for lesion segmentation.

FIG. 11 shows a system for streamlined spatial normalization methods, that avoids computationally-burdensome template construction and normalization steps. The system shown in FIG. 11 features a dual encoder-decoder network for the anatomy normalization for obtaining abnormal lesion segmentation, as shown in FIG. 10. For lesion segmentation, the illustrated system incorporates an additional abnormality cost, which is a difference between warped images of a healthy patient and warped images of a patient having the relevant pathology. These images are 3D images.

The network is optimized toward the maximization of the similarity as well as abnormality of lesions. In one embodiment, two ResNet-based U-Net (ResNet34/50-UNet) in a Keras deep learning framework are constructed for the entire network. But the last layer of decoder is modified to match the three channels of a deformable field.

CT images of both non-bleeding and bleeding patients, which represent the system's inputs, are preprocessed by two steps.

The first step is that of applying an invertible intensity transform to emphasize contrast. In the illustrated embodiment, this emphasizes image contrast between cerebrospinal fluid and the parenchyma.

The second step is a skull-stripping step. This includes extract the brain using a brain extraction tool with a fractional intensity threshold.

Using a CT template, the dual anatomy normalization network, which combined two ResNet-UNets, is alternately trained with the preprocessed CT volume of both the data set for the bleeding patient and the data set for the non-bleeding patient. Each ResNet-UNets is subsequently trained with and without a pretrained model using two different training solvers: a stochastic gradient descent solver and adaptive moment estimator. The base learning rate of weight filters is set at $10^{-3}$ and decreased by three steps in accordance with training epochs. In the inference step, the lesion overlaid atlas is converted to an original coordinate space by an inverse transformation matrix, calculated from spatial normalization.

Having described the invention and a preferred embodiment thereof, what is new and secured by Letters Patent is:

1. A method comprising annotating medical images in a database of medical images, said database including first and second sets of images, said first set consisting of images that are known to have lesions, and said second set consisting of images that are known to be free of lesions, wherein annotating said medical images comprises:
    using at least images that are stored in said database to determine values of first parameters and values of second parameters, said first parameters being for configuring a first image analysis component and said second parameters being for configuring a second image analysis component,
    wherein said first image analysis component is configured to produce an output based on an input image from said first set, said output including a synthetic normal image and lesion data, said synthetic normal image having been formed by modifying said input image to reduce an amount of data indicative of a lesion in said input image, said lesion data characterizing said lesion,
    wherein said second image analysis component is configured to discriminate between images from said second set and said synthetic normal image, and
    wherein determining values of said parameters results in parameters that hinder said second image analysis component in said discrimination and that also promote an ability to reconstruct said input image from said output of said first image analysis component, and
    processing each image of said first set using said first image analysis component to generate annotated images according to said lesion data output by said first image analysis component with said first image as input, said first image analysis component having been configured with said values of said first parameters.

2. The method of claim 1, wherein said synthetic normal image is one of a plurality of synthetic normal images and wherein said method further comprises using a computer-implemented training controller to determine values of first and second parameters for a parameterized discriminator that distinguishes real normal images, which are from normal patients, from said synthetic normal images, wherein said controller determines said values of said first parameters to reduce an aggregate measure of discriminability between real normal images and said synthetic normal images and said controller selects said values of said second parameters to increase said discriminability.

3. The method of claim 1, further comprising suppressing modification of said input image at points in said input image that are outside said lesion.

4. The method of claim 3, wherein suppressing said modification comprises comparing said first image to said second image.

5. The method of claim 1, further comprising obtaining said medical images from a set of images obtained by computerized tomography.

6. The method of claim 5, wherein the first image consists of a first region, which includes the lesion, and a second region, which excludes the lesion, and wherein the first and second regions differ in intensity.

7. The method of claim 1, further comprising obtaining said first set of images by magnetic resonance imaging.

8. The method of claim 7, wherein said first set includes a first image that consists of a first region, which includes the lesion, and a second region, which excludes the lesion, and wherein the first and second regions differ in intensity.

9. The method of claim 1, wherein determining values of said parameters comprises updating said values during the course of a plurality of iterations, wherein updating said values includes processing an image from said first set, using said first image analysis component to output a corresponding synthetic normal image and corresponding lesion data and, providing said synthetic normal image to said second image analysis component to predict whether said synthetic normal image is from said second set or a synthetic normal image, wherein said second image analysis component mistakenly identifies said synthetic normal image as being an image from said second set.

10. The method of claim 1, further comprising processing said synthetic normal image and said lesion data to produce a synthetic abnormal image and determining an extent to which said synthetic abnormal image differs from said abnormal image that was used as a basis for generating said synthetic normal image.

11. The method of claim 1, wherein said lesion data characterizes a spatial extent of a region occupied by said lesion.

12. The method of any of claim 1, wherein said lesion data comprises image data in the region.

13. The method of any of claim 1, wherein the first image processing component and the second image processing component each comprises an artificial neural network.

14. The method of claim 13, wherein determining the values of the parameters comprises performing an adversarial training procedure using a combined metric representing an overall ability to discriminate between the images of the normal set of images and the images formed by the first image analysis component and an ability to reconstruct images from the abnormal set from the outputs of the first image analysis component.

15. The method of claim 1, wherein said input image is an image of a patient having abnormal lesions, wherein said method further comprises receiving an age-specific template created by averaging normalized images over a population of healthy subject images in a certain age range and generating a delineation of a lesion using a statistical voxel comparison between a normalized image without abnormality or disease and without lesions.

16. The method of claim 15, further comprising segmenting the lesion, using two encoder-decoder networks to determine parameter values of transformation parameters for anatomical normalization and selecting the values of the transformation parameters to maximize a similarity measure between a warped image in a warped space and a source image in a source space, selecting a threshold value of the segmented lesion generated by analyzing statistical voxel comparison between the normalized images of patient with lesions and the normalized images of patients without lesions, and selecting the parameters of the inverse transformation to transform the lesion segment on the warped space into said source space.

17. The method of claim 1, further comprising using an encoder-decoder segmentation network training controller to determine values for the parameters of a parameterized segmentation module for delineating lesions from patients and selecting parameter values to reduce a pixel-level loss function between annotated images from initial seed data sets and the predicted images from a segmentation module and selecting updated annotation data sets by applying a likelihood value between representative density functions of seed annotation data and annotated lesions predicted from a previously trained segmentation module, wherein said loss function is selected from the group consisting of a cross-entropy and a Dice similarity coefficient.

18. The method of claim 1, wherein using said first image analysis component to generate said annotated images comprises segmenting and tagging abnormal lesions.

19. The method of claim 1, wherein using said first image analysis component to generate said annotated images comprises implementing multi-tasking annotation.

* * * * *